(12) United States Patent
Tracy et al.

(10) Patent No.: US 7,165,550 B1
(45) Date of Patent: Jan. 23, 2007

(54) CERVICAL ISOLATION AND DELIVERY APPARATUS

(75) Inventors: Timothy S. Tracy, Morgantown, WV (US); Douglas D. Glover, Morgantown, WV (US); Patrick S. Callery, Morgantown, WV (US); Andrew P. Soisson, Morgantown, WV (US); James E. Smith, Bruceton Mills, WV (US)

(73) Assignee: West Virginia University, Morgantown, WV (US)

( * ) Notice: Subject to any disclaimer, the term of this patent is extended or adjusted under 35 U.S.C. 154(b) by 368 days.

(21) Appl. No.: 10/379,078

(22) Filed: Mar. 3, 2003

Related U.S. Application Data (63) Continuation-in-part of application No. 09/649,170, filed on Aug. 25, 2000, now Pat. No. 6,526,980.

(60) Provisional application No. 60/150,785, filed on Aug. 26, 1999.

(51) Int. Cl.
*A61F 6/06* (2006.01)

(52) U.S. Cl. ...................... 128/837; 128/838

(58) Field of Classification Search ......... 128/830–841
See application file for complete search history.

(56) References Cited

U.S. PATENT DOCUMENTS

| 436,861 | A | * | 9/1890 | Sherwood | 128/835 |
|---|---|---|---|---|---|
| 614,895 | A | * | 11/1898 | Rober | 128/841 |
| 705,285 | A | * | 7/1902 | Overton | 128/841 |
| 2,818,856 | A | * | 1/1958 | Kohl | 128/838 |
| 3,590,816 | A | * | 7/1971 | Rosenthal | 128/840 |
| 4,398,532 | A | * | 8/1983 | Sweeney, III | 128/838 |
| 4,785,804 | A | | 11/1988 | Tlapek et al. | 128/841 |
| 4,832,052 | A | | 5/1989 | Mohajer | 128/839 |
| 4,862,899 | A | | 9/1989 | Bucaro | 128/749 |
| 4,993,432 | A | | 2/1991 | Shields et al. | 128/838 |
| 5,044,376 | A | | 9/1991 | Shields | 128/837 |
| 5,123,424 | A | | 6/1992 | Koch | 128/841 |

(Continued)

OTHER PUBLICATIONS

Product Literature titled ZUI (Zinnanti Uterine Injector); webpage.

*Primary Examiner*—Michael A. Brown
(74) *Attorney, Agent, or Firm*—Steptoe & Johnson, PLLC (57) ABSTRACT

A cervical isolation and delivery apparatus having a cervical cap removably connected to a syringe such that a bottom opening of the cervical cap is in communication with an internal chamber of the syringe. The syringe is an elongated hollow tube with an elongated rod slidable disposed within an internal chamber of the elongated hollow tube. The cervical cap is removably connected to an application end of the elongated hollow tube such that upon insertion of the apparatus into a patient's vagina, the cervical cap covers the patient's cervix while protecting the tissue surrounding the cervix. The patient's cervix is treated by placing medication, e.g., one or more therapeutic agents, in the elongated hollow tube such that the elongated rod is in an extended position, inserting the apparatus into a patient's vagina, positioning the cervical cap over the patient's cervix, and pushing the elongated rod through the internal chamber of the elongated hollow tube until it is in a retracted position, thereby expelling the medication from the internal chamber into and through the cervical cap and into contact with the patient's cervix. The cervical cap covers and isolates the cervix thereby preventing the medication from leaking from the cervical area and irritating surrounding tissue.

6 Claims, 6 Drawing Sheets

U.S. PATENT DOCUMENTS

| | | | |
|---|---|---|---|
| 5,364,375 A | 11/1994 | Swor | 604/278 |
| 5,536,243 A | 7/1996 | Jeyendran | 600/35 |
| 5,823,954 A * | 10/1998 | Chaffringeon | 600/367 |
| 5,980,804 A | 11/1999 | Koch | 264/222 |
| 6,139,538 A | 10/2000 | Houghton et al. | 604/515 |

* cited by examiner

CERVICAL ISOLATION AND DELIVERY APPARATUS

RELATED APPLICATIONS

This application is a continuation-in-part of U.S. patent application Ser. No. 09/649,170, filed Aug. 25, 2000 now U.S. Pat. No. 6,526,980, that claims the benefit of U.S. patent application 60/150,785, filed Aug. 26, 1999.

BACKGROUND OF THE INVENTION

1. Field of the Invention

This invention relates to medical instruments, and more specifically, to a medical instrument for isolating a patient's cervix.

2. Related Art

Currently, therapeutic agents, e.g. misoprostol, are delivered to a human cervix either by inserting a tablet or gel directly into a patient's vagina, which exposes both the vagina and cervix to the agent, or by direct injection of the agent into the cervix with a needle, which can be extremely painful to the patient. The disadvantage with these procedures, however, is that several agents designed for drug therapy to the cervix are either systemically toxic or cause irritation to the vagina or outer vulva. Alternatively, other agents given for cervical maladies are creams which also can be inserted into the vagina. The disadvantage with creams is that they often leak out onto the vulva and become extremely irritating and painful.

Therefore, a cervical agent isolation and delivery apparatus is needed that provides for the direct administration and delivery of therapeutic agents to a patient's cervix, e.g., anesthetics, anti-virals, anti-neoplastics and cervical ripening agents, while minimizing vaginal and systemic exposure to the agent. Since the cervix is not as highly vascularized as the vagina, direct administration to the cervix of a therapeutic agent would reduce systemic exposure of the agent to other areas of the patient since less of the agent would be distributed to the body and the desired organ (cervix) will be specifically targeted.

One example of conventional methods of drug delivery to a patient's cervix involves the administration of anesthetic agents to reduce pain and discomfort prior to cervical dilation or biopsy. Currently, there are no other established methods for administering anesthetic agents to a patient's cervix other than direct injection of the anesthetic via a needle and syringe. Most patient's report this injection to be more painful and uncomfortable than the procedure (which itself is uncomfortable and sometimes painful). Thus, the majority of women, and their physicians, choose to forego the administration of any anesthetic agent and simply endure the pain associated with the procedure itself.

As another example of conventional methods for cervical drug delivery, Misoprostol, a tablet traditionally used to prevent non-steroidal anti-inflammatory drug induced ulcers in a patient's stomach, is sometimes delivered to the cervix. However, Misoprostol is contra-indicated on its label for use with a pregnant patient because of its effect for inducing labor. In reality, however, physicians often apply Misoprostol for its off-label use in the promotion of cervical ripening in pregnancy wherein the physician directly applies a Misoprostol tablet to a patient's cervix in order to induce cervical ripeness, thereby inducing labor. There are many disadvantages with using Misoprostol for this off-label use. First, this topical use is directly counter to the drug's allowed use. Second, the tablet form of Misoprostol is intended for oral ingestion only—not as a topical agent. Therefore, the tablet form occasionally does not dissolve in a vagina. In addition the tablet may be difficult to position properly so as to directly contact the cervix. Lastly and most importantly, the proper dosage of Misoprostol has not been ascertained or even studied because this use of Misoprostol is a non-labeled use. Therefore, physicians typically use a "hit or miss" dosage until the desired effect is achieved.

Another type of device used in connection with covering a patient's cervix is the cervical cap. For example, the Prentif Cervical Cap® covers a patient's cervix and is used as a barrier method of contraception. Similarly, the Today® contraceptive sponge is a sponge-like device shaped to fit over a patient's cervix, thereby also serving as a physical contraceptive barrier. However, the Today® sponge also contains nonoxynol-9 (a spermicidal agent) which is released into the vagina to assist in preventing contraception. A second type of cervical cap is the Instead® (cervical) Cap which is a flexible ring connected to a flexible plastic sac-like reservoir. The ring fits around a patient's cervix wherein the reservoir collects the patient's menstrual flow. This device is not designed to fit closely around the cervix.

Other types of devices used in connection with a patient's cervix consist of a catheter that is inserted through the cervix and into the uterus to allow administration of therapeutic agents to enhance the contrast seen in the uterus during an ultrasound procedure. An example of this type of device is the Zinnanti Uterine Injector® which is a catheter having a cervical stop to prevent inserting it too far into the patient's uterus. This device is available in 2 and 4 mm sizes, and in dual lumen designs allowing delivery of an agent through one lumen and delivery of air to a balloon-like structure through the second lumen to prevent it from coming out of the uterus.

While the various devices and methods are aimed either at isolating or treating a patient's cervix, none provides an effective means to both deliver a medicine to the patient's cervix while simultaneously isolating the cervix from surrounding anatomical structures. There remains a need for a medical instrument that allows a physician to isolate a patient's cervix while administering a treatment thereto.

SUMMARY OF THE INVENTION

The present invention solves the problems encountered with conventional methods of treating a patient's cervix by providing an apparatus for isolating the patient's cervix and delivering a medication, e.g., a therapeutic agent, directly to the cervix while protecting the surrounding tissue of the patient. One aspect of the invention is an elongated hollow tube having an elongated rod slidably disposed within an internal chamber of the elongated hollow tube. A cervical cap is connected to the distal end of the elongated hollow tube such that upon insertion of the apparatus into a patient's vagina, the cervical cap covers and isolates the patient's cervix from the surrounding tissue. The cervical cap is either permanently fixed to, or in the alternative, is removably attached to, the distal end of the elongated hollow tube. The patient's cervix is treated by placing medication, e.g., a therapeutic agent, in the elongated hollow tube such that the elongated rod is in an extended position, inserting the apparatus into a patient's vagina, positioning the cervical cap over the patient's cervix, and pushing the elongated rod through the internal chamber of the tube until it is in a retracted position, thereby expelling the medication from the tube into and through the cervical cap and into contact with the patient's cervix. The cervical cap covers and isolates the cervix thereby preventing the medication from leaking from the cervical area and irritating surrounding tissue.

Another aspect of the invention is a cervical isolation and delivery kit having component parts capable of being assembled by either a healthcare provider or a patient in order to isolate the patient's cervix prior to delivering one or more cervical, therapeutic agents. The kit contains an elongated hollow tube adapted for receiving and storing the one or more cervical agents, an elongated rod adapted to be inserted through and slidably disposed within the elongated hollow tube, thereby forcing the one or more cervical agents from the elongated hollow tube, and one or more cervical caps adapted to be removably connected to a distal end of the elongated hollow tube for isolating and delivering the one or more cervical agents directly to the patient's cervix. The one or more cervical caps have varying sizes and are connected to the elongated hollow tube at various angles for accommodating the anatomical differences between patients.

Another aspect of the invention is a method of dispensing one or more cervical, therapeutic agents to a patient's cervix, including the steps of: (a) inserting a cervical isolation and delivery apparatus into a patient's vagina, the apparatus having an elongated rod slidably disposed within an internal chamber of an elongated hollow tube and a cervical cap connected to a distal end of the apparatus for isolating a patient's cervix, wherein the cervical cap has a top and a bottom that is connected to the distal end of the elongated hollow tube; (b) positioning the cervical cap of the apparatus over the patient's cervix; and (c) pushing the elongated rod through the internal chamber of the elongated hollow tube, thereby forcing the one or more cervical agents from the elongated hollow tube into the cervical cap and in direct contact with the patient's cervix while protecting the tissue surrounding the patient's cervix.

A feature of the invention is an angled base integral to the bottom of the cervical cap such that the cervical cap is attached to the elongated hollow tube at an angle.

Another feature of the invention is that the diameter of the elongated hollow tube tapers near its application end having the cervical cap.

Another feature of the invention is that elongated hollow tube has a threaded neck at its distal end for receiving a cervical cap, thereby making the cervical cap removable.

Another feature of the invention is that the base of the cap has a smooth internal surface and a threaded exterior surface.

Another feature of the invention is that the elongated rod has a primary expelling surface and a secondary expelling surface.

Another feature of the invention is that the primary expelling surface has a diameter about the same as the inside diameter of the elongated hollow tube.

Another feature of the invention is that the secondary expelling surface extends from the primary expelling surface and has a diameter about the same as the inside diameter of the base of the cervical cap.

Another feature of the invention is that the secondary expelling surface has a height about the same as the height of the base of the cervical cap and the neck of the elongated hollow tube, such that when the elongated rod is pushed all the way through the internal chamber of the elongated hollow tube toward the distal end, the secondary expelling surface extends through the neck of the elongated hollow tube and the base of the cervical cap and sits about flush with the bottom of the cervical cap.

Another feature of the invention is that the cervical cap has a smooth rim along its outer edge.

An advantage of the invention is that the cervical cap is angled and is available in multiple sizes, thereby making it easier for the user to isolate the patient's cervix and to custom fit the cervical cap for a specific patient.

Another advantage of the invention is that the lip around the open end of the cervical cap eliminates sharp edges and provides a seal around the patient's cervix.

Another advantage of the invention is that little or no therapeutic agent accumulates in the transition area between the elongated hollow tube and the cervical cap because the smooth interior surface of the base of the cervical cap extends down into the neck of the hollow elongated tube.

Another advantage of the invention is that the second expelling surface delivers the one or more cervical agents directly into the cervical cap because the second expelling surface sits flush, or almost flush, with the bottom of the cervical cap.

Another advantage of the invention is that the elongated rod passes through the internal chamber of the elongated hollow tube with little resistance until just prior to expelling the one or more cervical agents from the elongated hollow tube.

Another advantage of the invention is a plurality of ridge or grooves on the interior surface of the elongated hollow tube for regulating the flow of a therapeutic agent.

BRIEF DESCRIPTION OF THE DRAWINGS

The present invention is described with reference to the accompanying drawings. In the drawings, like reference numbers indicate identical or functionally similar elements. Additionally, the left-most digit(s) of a reference number identifies the drawing in which the reference number first appears.

EMBODIMENTS OF THE INVENTION

Figure 1:
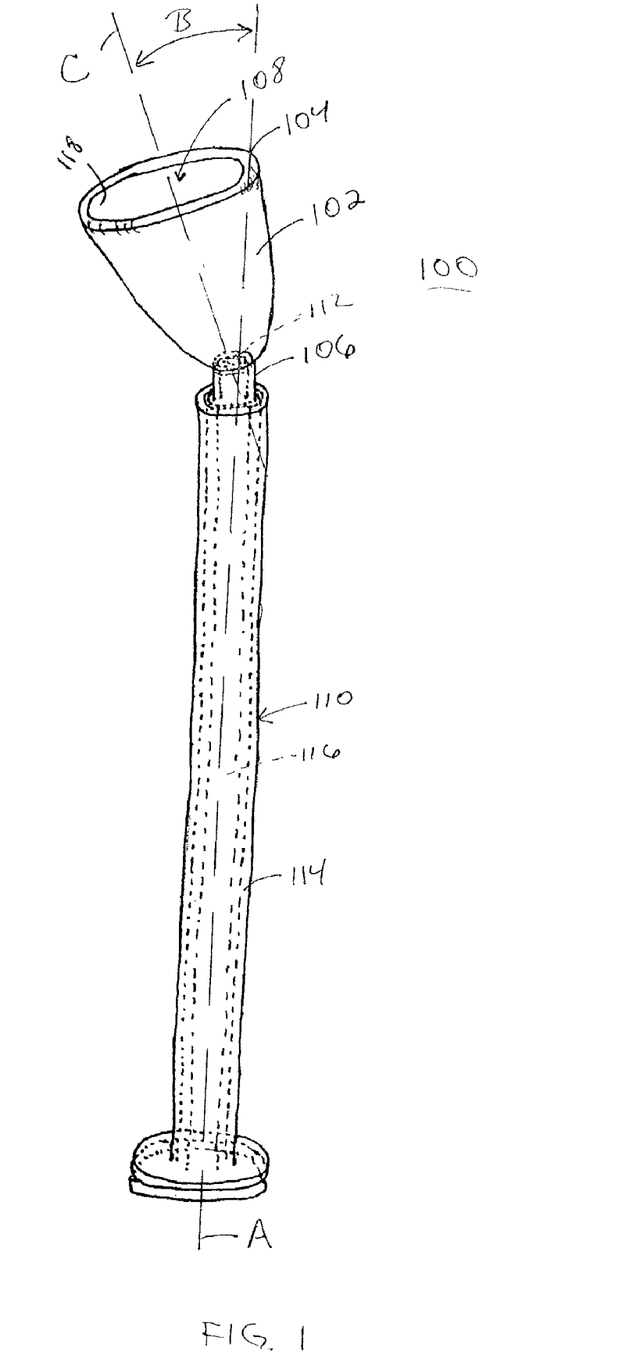
FIG. 1 is a perspective view of the cervical isolation and delivery apparatus of the present invention.

The present invention uses a cervical isolation device (CID) 100 to isolate and treat a patient's cervix. Nonlimiting examples of cervical treatments include delivering one or more therapeutic agents to the cervix, performing a biopsy or other surgery, or collecting cervical cells for analytical testing, e.g., PAP smears. Therapeutic agents include, without limitation, anesthetics, anti-virals, anti-neoplastics, and cervical ripening agents, e.g., Misoprostol. The CID 100 preferably includes a cervical cap 102 removably connected to an end of a syringe 110.

Cervical Cap:

The cervical cap 102 preferably is shaped e.g., bell-shaped, such that upon insertion of the CID 100 in a patient's vagina, the cervical cap 102 surrounds and covers the patient's cervix thereby isolating the cervix from the surrounding tissues. See FIGS. 1 and 4. Once isolated, the cervix is treated without affecting surrounding tissue. To this end, the cervical cap 102 has a front opening 108 that is wider than, and tapers to, a narrower bottom opening 112. A hollow base 106 extends from the bottom opening 112 of the cervical cap 102 and provides the means for attaching the cervical cap 102 to the syringe 110. The cervical cap 102 optionally, but preferably, has a smooth lip 104 at its front opening 108 that makes inserting the CID 100 easier and less painful for the patient. The lip 104 also creates a seal around the cervix once the cervical cap 102 is positioned properly.

The cervical cap 102 preferably is angled in relation to the syringe 110, thereby facilitating proper positioning of the cervical cap 102 over the cervix. This angling is shown on FIGS. 1 and 4 wherein the center longitudinal axis C of the cervical cap 102 is offset from the center longitudinal axis A of the syringe 110 by an angle B. The angling of the cervical cap 102 helps the user locate and isolate the cervix because the angle accommodates the typically angled nature of the cervix in relation to the vaginal canal through which the CID 100 is inserted.

Figure 4:
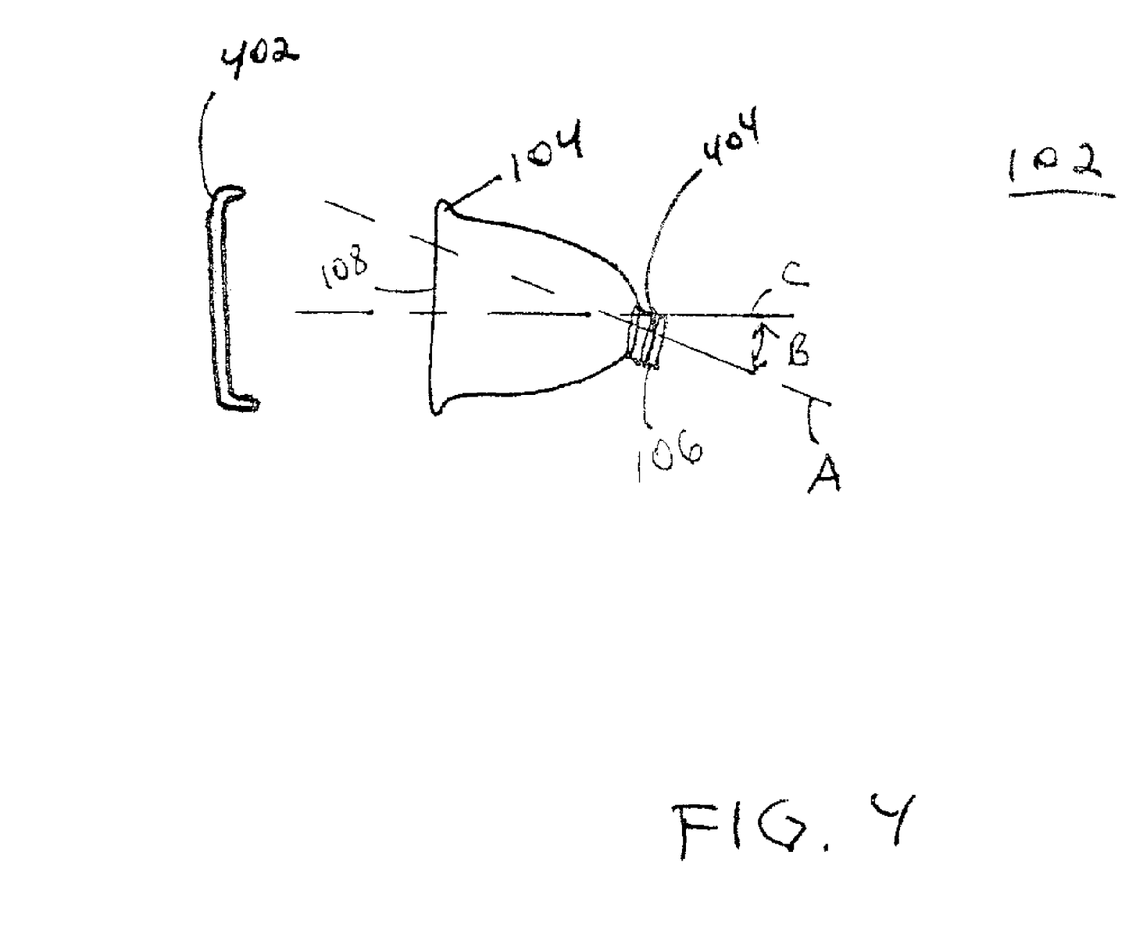
FIG. 4 is a perspective view of the cervical cap.

In order to create the angling, the base 106 extends from the bottom of the cervical cap 102 at angle B. The base 106 preferably is integrally connected to the bottom of the cervical cap 102, but alternatively may be detachably connected by means known to one having ordinary skill in the art. For example, in an embodiment in which the base 106 is detachably connected to the cervical cap 102, bases 106 of various lengths and shapes may be used to further personalize the CID 100 for each individual patient. Likewise, the angle at which the cervical cap 102 and base 106 are connected preferably is fixed, but also may be adjustable by including a swivel apparatus between the cervical cap 102 and the base 106 which allows the cervical cap 102 to swivel about the longitudinal axis A of the syringe 110. The cervical cap 102 may be sold as part of a kit containing several cervical caps 102 of varying sizes and having various angles C thereby accommodating each patient's anatomy.

The base 106 is hollow and has an aperture along its length that is contiguous with the bottom opening 112 in the bottom of the cervical cap 102. The interior surface of the base 106 preferably is smooth to facilitate the transfer of the one or more cervical agents, while the exterior surface of the base 106 preferably is threaded 404 for removably connecting the cervical cap 102 to the syringe 110. Alternative connecting means include pressure-fitting, conventional locking mechanisms, fasteners, adhesives, and other means known to one of ordinary skill in the art.

The design and use of a base 106 is optional. In an alternative embodiment, the cervical cap 102 may be fixed to the end of the elongated hollow tube 114 such that the bottom opening 112 of the cervical cap 102 is connected directly to the interior chamber 210 of the elongated hollow tube 114. In this embodiment, there is no base 102. However, the cervical cap 106 may still swivel or rotate in relation to the elongated hollow tube 114 and may be removably attachable to the elongated hollow tube 114.

In an alternative embodiment, the cervical cap 102 optionally may include a cover 402. The cover 402 may either be a flip-up cover that is hingedly connected to one side of the cervical cap 102 or it may be completely detachable as shown in FIG. 4. The cover 402 snap fits over the lip 104 of the front opening 108 of the cervical cap 102. Accordingly, the cover 402 is made of rubber or a semi-rigid plastic. The cover 402 is useful because it allows the cervical cap 102 to function as a collection and storage means for cell or tissue samples gathered from the cervix as described in further detail below.

In the preferred embodiment, the cervical cap 102 has an overall length of about 1.484 inches, a front opening 108 of about 1.328 inches, a bottom opening 112 of about 0.238 inches, a base 106 length of about 0.22 inches, and an angle C of about 15 degrees. The cervical cap 102 preferably is made of a semi-rigid plastic, but may be made of alternative materials that will impart to the cervical cap 102 the necessary combination of rigidity and flexibility. Alternative materials include, without limitation, rubber and synthetic polymers or other similar composite materials. In an alternative embodiment, the cervical cap 102 may be collapsed when inserted into a patient and then expanded once in place, thereby reducing the possibility of patient discomfort as the CID 100 is inserted into and through the patient's vagina.

Syringe:

The syringe 110 preferably includes an elongated hollow tube 114 with an elongated rod 116 slidably disposed therein. The elongated hollow tube 114 has a tube body 204 having an application end 202, a front end 206, and an interior chamber 210 for holding one or more therapeutic agents. See FIG. 2. The elongated hollow tube 114 also has a neck 212 extending from its application end 202 along the longitudinal axis A and a stabilizing flange 208 positioned at its front end 206.

Figure 2:
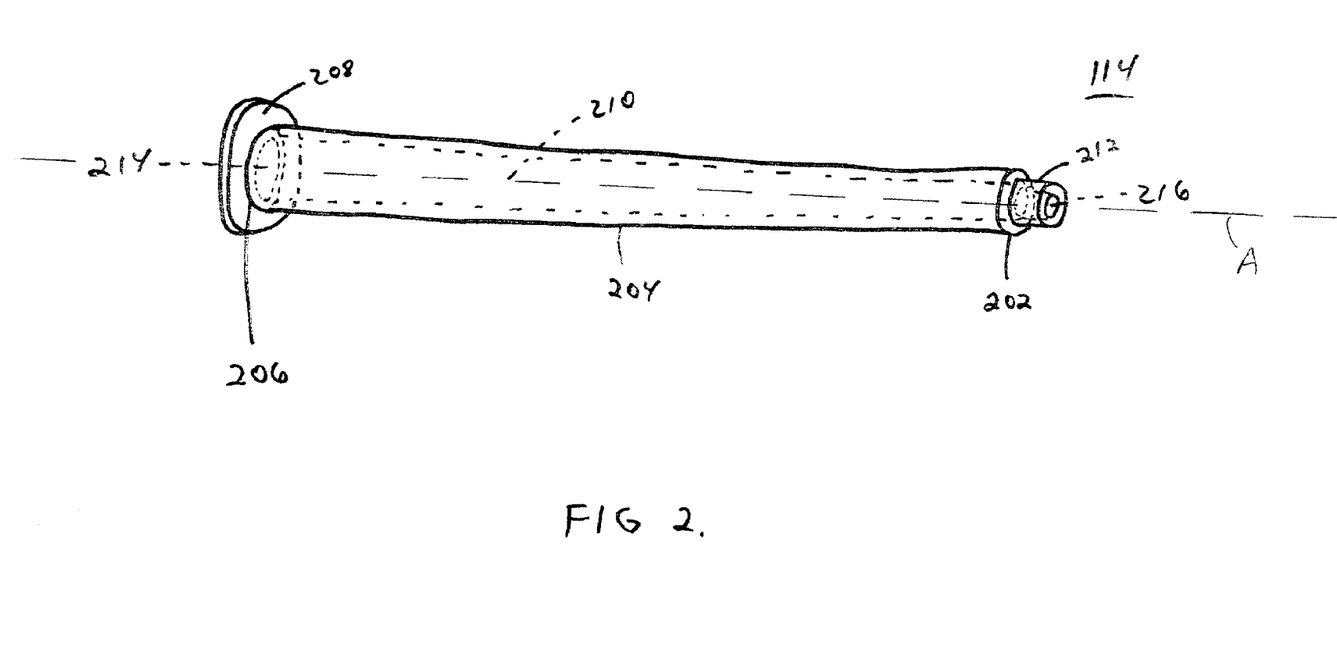
FIG. 2 is a perspective view of the elongated hollow tube.

The tube body 204 of the elongated hollow tube 120 preferably tapers along its length such that its diameter is greatest at its front end 206 and least at its application end 202. The tapering provides a means for regulating the dispensing of therapeutic agents by permitting the elongated rod 116 to slide through the interior chamber 210 of the elongated hollow tube 114 with minimal resistance in the beginning until the elongated rod 116 approaches the application end 202 of the elongated hollow tube 120. The tapering of the tube body 204 of the elongated hollow tube 114 makes delivery of the one or more cervical agents easier for the user of the CID 100 because he or she easily can slide the elongated rod 116 through the interior chamber 210 of the tube body 204 until just before the one or more therapeutic agent(s) is expelled from the application end 202 of the elongated hollow tube 114. The user also has additional control over when a drug is expelled from the application end 202 of the elongated hollow tube 114 because additional pressure is needed to force the elongated rod 116 through the narrowest portion of the elongated hollow tube 114. Furthermore, the tapering of the elongated hollow tube 120 is optional wherein one of ordinary skill in the relevant arts can design a CID 100 of the present invention without such tapering.

The elongated hollow tube 114 narrows to a hollow neck 212, having an aperture 216, at its application end 202. The interior surface of the aperture 216 in the neck 212 preferably is threaded for receiving the threads 404 of the base 106 of the cervical cap 102, thereby establishing a means for connecting the cervical cap 102 to the application end 202 of the elongated hollow tube 114 of the syringe 110. The length of the neck 212 preferably is about the same as the length of the base 106. Thus, the entire inner surface of the neck 212, which is threaded, is lined by the smooth inner surface of the base 106 when the cervical cap 102 is connected to the elongated hollow tube 114. As a result, there is an efficient transfer of the one or more therapeutic agents from the elongated hollow tube 114 into the cervical cap 102. This efficient transfer is imperative because therapeutic agents often are dosed based upon the presumption of near 100% delivery of the active ingredients of the therapeutic agents to the patient. While the cervical cap 102 and elongated hollow tube 114 of the syringe 110 preferably are connected by threads, they may be connected by alternative means, such as pressure fit, snaps, adhesives, an aperture and a pin, or other connecting means known to one of ordinary skill in the art.

The front end 206 of the elongated hollow tube 114 preferably has a stabilizing flange 208 extending perpendicularly away from the tube body 204. The diameter of the flange 208 is greater than the diameter of the elongated hollow tube 114 at its front end 206. The flange 208 makes sliding the elongated rod 116 through the interior chamber 210 of the elongated hollow tube 114 easier because it creates a place for the user to place his or her fingers while pushing the elongated rod 116 with his or her thumb. The use of a flange 208 is optional, wherein it is readily apparent to one of ordinary skill in the relevant art to design a CID 100 of the present invention without such a flange 208.

Figure 3:
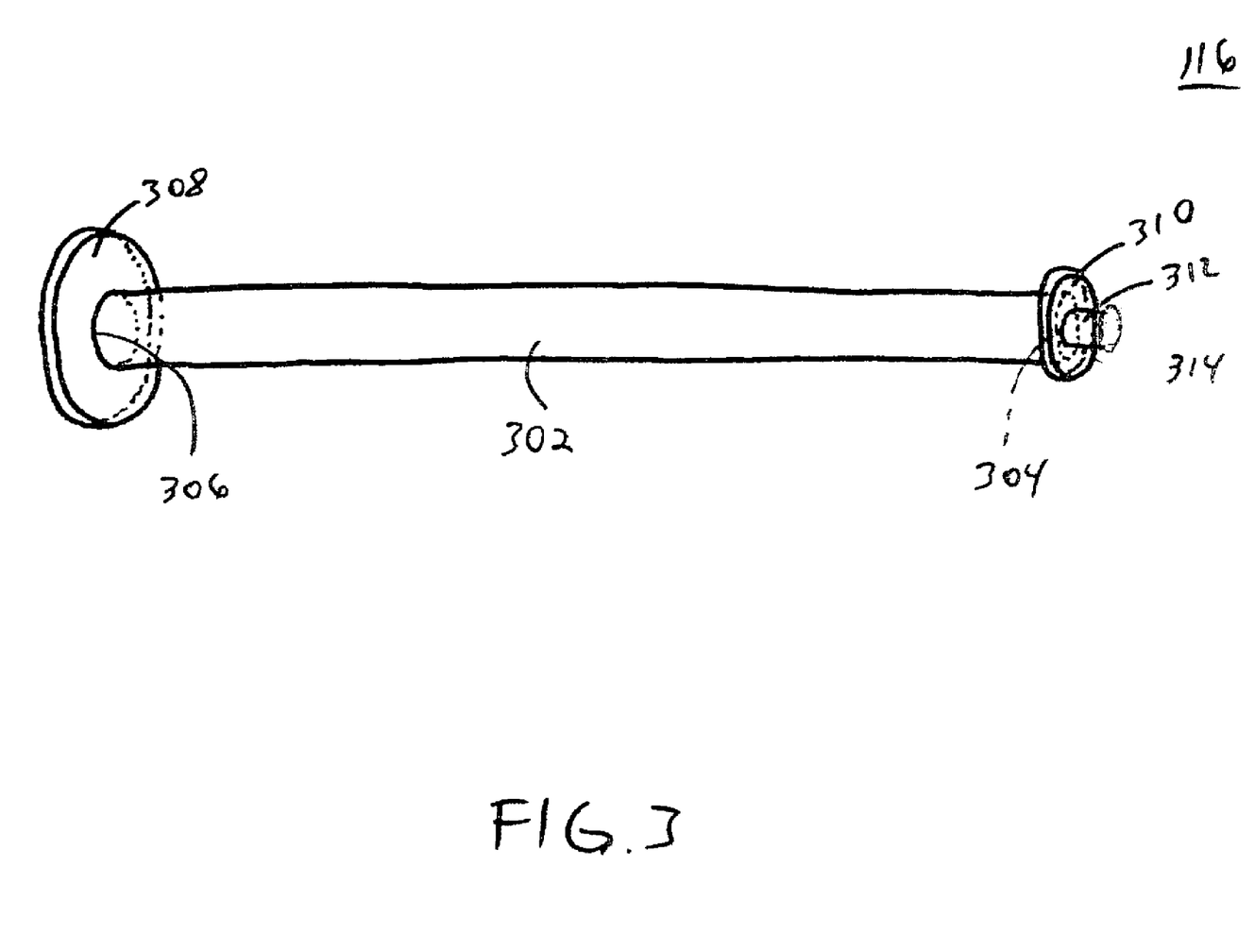
FIG. 3 is a perspective view of the elongated rod.

The elongated rod 116, shown in detail on FIG. 3, is adapted to be slidably disposed within the elongated hollow tube 114 of the syringe 110. The elongated rod 116 has cylindrical body 302 having an application end 304, an engaging end 306, and a length that is slightly longer than the length of the elongated hollow tube 114. Similar to the elongated hollow tube 114, the engaging end 306 of the elongated rod 116 includes a flange 308 that preferably is round and has a diameter about equal to the diameter of the flange 208 of the elongated hollow tube 114. The flange 308 provides a means for a user to apply pressure to the elongated rod 116 thereby sliding the elongated rod 116 through the interior chamber 210 of the elongated hollow tube 114. Furthermore, the flange 308 is also optional wherein one of ordinary skill in the relevant art can design a CID 100 of the present invention without such a flange 308.

When sliding the elongated rod 116 through the elongated hollow tub 114, the application end 304 of the elongated rod 116 forces the one or more therapeutic agents through the elongated hollow tube 114 and into the cervical cap 102. Specifically, the application end 304 of the elongated rod 114 preferably has a first expelling surface 310 and a second expelling surface 312, with the second expelling surface 312 being optional. The first expelling surface 310 is a flange positioned at the end of the application end 304 of the cylindrical body 302 and has a diameter approximately the same as the diameter of the internal chamber 210 of the elongated hollow tube 114 near its application end 202 just below the neck 202. The first expelling surface 310 preferably rests flush against the bottom of the neck 212 of the elongated hollow tube 114 when the elongated rod 116 is slid completely forward (toward the application end 202 of the elongated hollow tube 114) within the interior chamber 210 of the elongated hollow tube 114, thereby efficiently forcing the one or more cervical agents into the neck 212.

The second expelling surface 312 is preferably a cylindrical extension of the elongated rod 116 having a diameter smaller than the diameter of the first expelling surface 310. The second expelling surface 312 extends upward from the first expelling surface 310 and into the neck 212 of the elongated hollow tube 114. The diameter of the second expelling surface 312 preferably is about equal to the diameter of the aperture in the base 106 of the cervical cap 102 such that the second expelling surface 312 efficiently forces all of the one or more therapeutic agents through the base 106 and into the cervical cap 102. In addition, the second expelling surface 312 preferably has a length about the same as the length of the neck 212 of the elongated hollow tube 114 such that the top 314 of the second expelling surface 312 fits flush with the bottom opening 112 of the cervical cap 102 when the elongated rod 116 is slid completely forward within the interior chamber 210 of the elongated hollow tube 114. As stated above, the use of a second expelling surface 312 is optional, wherein it would be readily apparent to one of ordinary skill in the relevant art to design a CID 100 of the present invention having only a first expelling surface 310 such as in a conventional syringe.

Figure 5:
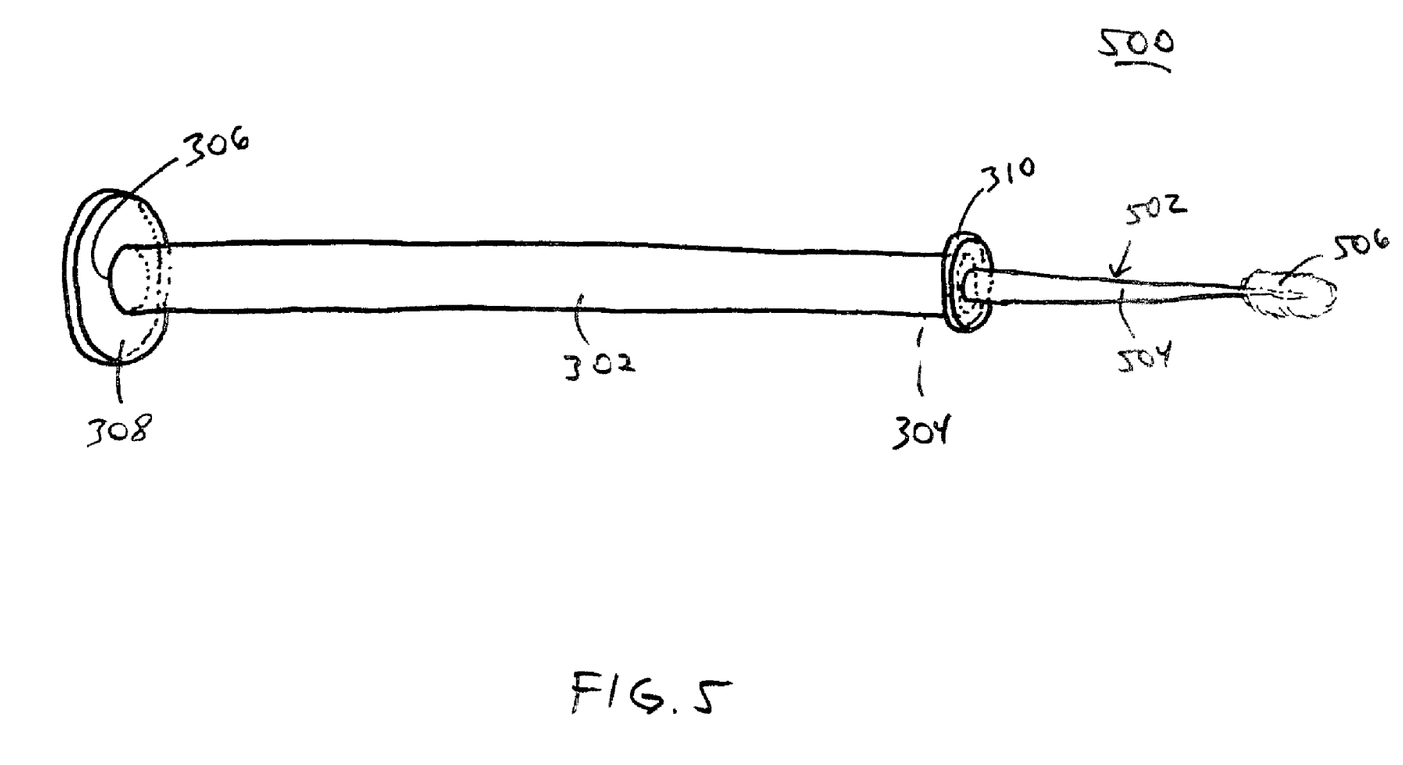
FIG. 5 is a perspective view of an alternative elongated rod.

In an alternative embodiment shown in FIG. 5, an elongated rod 500 is adapted to be slidably disposed within the elongated hollow tube 114 of the syringe 110. As described above, the elongated rod 500 has cylindrical body 302 having an application end 304, an engaging end 306, a length that is slightly longer than the length of the elongated hollow tube 114, and a flange 308. The alternative elongated rod 500 also includes a means for gathering cell samples 502 from a patient's cervix. The preferred means for gathering cell samples 502 is a rod 504 having a first end and a second end. The first end is secured to the top surface of the first expelling surface 310, while the second end has a brush 506 used to scrape or rub cells from a patient's cervix.

The cervical cap 102 in this alternative embodiment optionally, but preferably, includes a cap cover 402 to protect any cells collected and stored in the cervical cap 102. Also, in this alternative embodiment the elongated rod 116 rotates freely within the interior chamber 210 of the elongated hollow tube 114. This is accomplished either by slightly increasing the diameter of the elongated hollow tube 114 at its application end 202, or slightly decreasing the diameter of the elongated rod 116. The rotation of the elongated rod 116 is important because it allows the brush 506 to scrap or rub the cervix tissue, thereby collecting sample cells. In addition, the length of the means for gathering cells 502 is preferably less then the length of the cervical cap 102 in order to accommodate the closing of a cap cover 402 on the front end 108 of the cervical cap 102.

In the preferred embodiment, the elongated hollow tube 114 is of a sufficient length such that the cervical cap 102 extends through a patient's vagina to reach and cover the patient's cervix when the elongated hollow tube 114 is inserted into the patient's vagina. The length of the elongated hollow tube 114 preferably is fixed, but alternatively may be variable, i.e., telescoping. The elongated hollow tube 114 has a preferred length of about 6.75 inches, a flange 208 diameter of about 1.25 inches, and a neck 212 diameter of about 0.463 inches. Furthermore, the elongated rod 116 has a preferred length of about 6.932 inches, a flange 308 diameter of about 1.25 inches, a first expelling surface 310 diameter of about 0.510 inches, and a second expelling surface 312 diameter of about 0.228 inches.

The elongated hollow tube 14 and elongated rod 116 preferably are made of a semi-rigid plastic, but may be made of alternative materials having the desired rigidity and flexibility. Alternative materials include, without limitation, rubber, and synthetic polymers or other similar composite materials.

Figure 6:
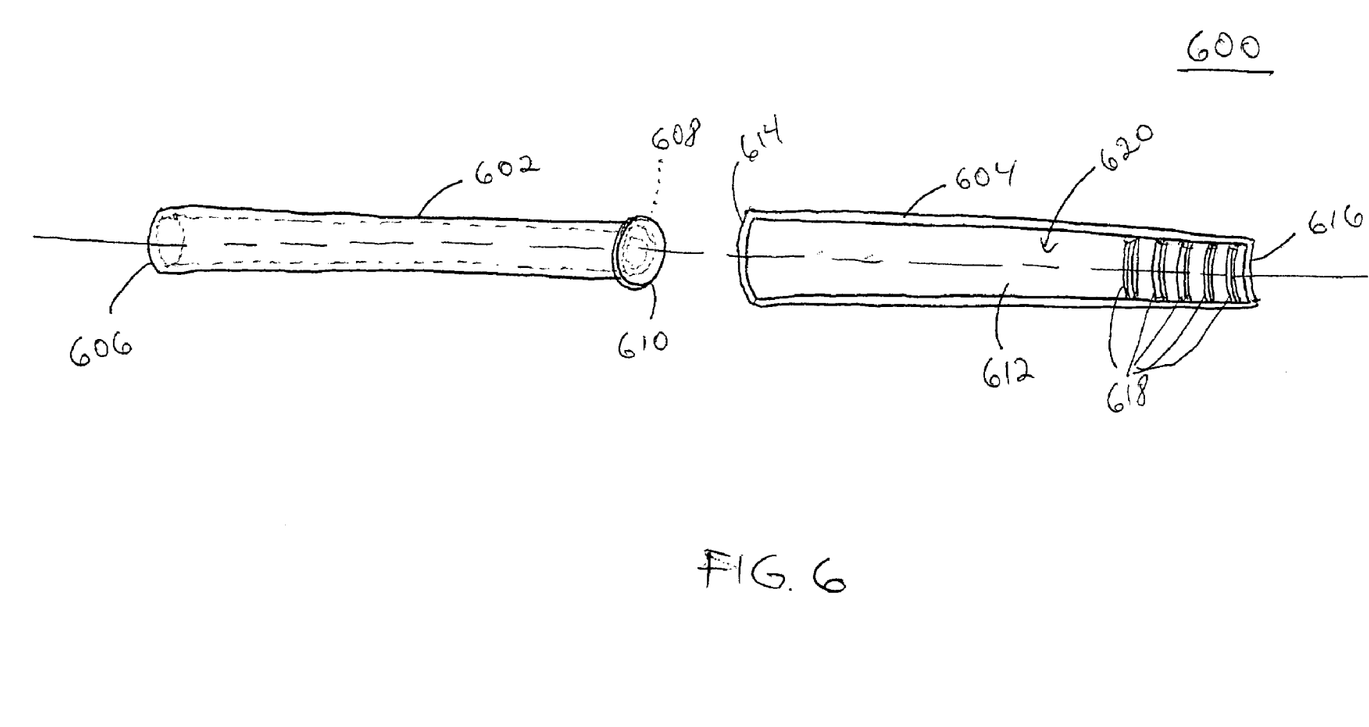
FIG. 6 is a perspective view of an alternative syringe showing a cut-away view of an alternative elongated hollow tube.

An alternative embodiment of the syringe 600 is shown in FIG. 6. In this alternative embodiment, the elongated hollow tube 604 has a front end 614 and one or more ridges 618, or protrusions, on its interior surface 612 near its application end 616. The ridges 618 are small flanges that extend into the internal chamber 620 of the elongated hollow tube 604 a predefined distance. For convenience purposes only, the ridges 618 are shown as rings, each of which extends into the internal chamber 620 as a band on the interior surface 612 of the elongated hollow tube 604. FIG. 6 shows a cut-away of the elongated hollow tube 604 in order to show the ridges 618 more clearly. In addition, if multiple ridges 618 are used, the ridges 618 are preferably equally spaced apart, but this is for convenience. It would be readily apparent to one of ordinary skill to space adjacent ridges 618 at varying distances.

Also in this alternative embodiment, an elongated rod 602, having a front end 606 and an expelling surface 610 at its application end 608 that is a flange having a shape equal to that of the internal chamber 620 of the elongated hollow tube 604. The expelling surface 610 of the elongated rod 602 and the ridges 618 of the elongated hollow tube 604 provide a user with a means for regulating the flow of a therapeutic agent from the application end 616 of the syringe 600. That is, as a user pushes the elongated rod 602, the flange engages the ridges 618 in succession, stopping the movement of the elongated rod 602 each time the expelling surface 610 contacts a ridge 618. This means for regulating is an alternative to the tapering of the elongated hollow tube 114 described above.

In addition, the use of ridges 618 is for convenience purpose only. It would be readily apparent to one of ordinary skill in the relevant art to use a comparable means for regulating the speed and flow of a therapeutic agent from the application end 616 of the syringe 600. For example, alternative means for regulating include, but are not limited to, protruding bumps on, or grooves or indentations in the interior surface 612 of the internal chamber 620. Thus, as the expelling surface 610 moves over the bumps, grooves, or indentations, the edges of the expelling surface 610 engages the bumps, grooves, or indentations and stops movement of the elongated rod 602.

Method of Use:

In a preferred method of use, the cervical cap 102 of the CID 100 isolates a patient's cervix such that one or more therapeutic agents can be delivered directly thereto. Prior to inserting the CID 100, one or more therapeutic agents are placed inside the internal chamber 210 of the elongated hollow tube 114 with the elongated rod 116 being in an extended position. The one or more therapeutic agents preferably are placed inside the internal chamber 210 of the elongated hollow tube 114 through its application end 202, but alternatively may be introduced through its front end 206. In addition, while therapeutic agents preferably are transferred from the syringe 110 to the cervical cap 102, they alternatively may be directly applied to the interior surface 118 of the cervical cap 102. For example, the manufacturer may embed therapeutic agents in the cervical cap 102 at the time of manufacture, or healthcare professionals or patients may manually apply therapeutic agents to the interior surface 118 of the cervical cap 102 prior to use.

Therapeutic agents frequently are formulated as ointments or gels and often are packaged in tubes. In the event that the desired therapeutic agent(s) are in a tube having a threaded front end, the therapeutic agent(s) can be inserted through the application end 202 of the elongated hollow tube 114 by screwing the threaded end of the tube into the neck 212 of the elongated hollow tube 114. Thus, a preferred method of introducing the one or more cervical agents into the internal chamber 210 of the elongated hollow tube 114 is to screw the front end of the tube containing the one or more cervical agents onto the neck 212 of the elongated hollow tube 114 and squeezing the tube until the desired amount of cervical agent(s) is introduced into the internal chamber 210 of the elongated hollow tube 114.

As with conventional syringes, the application end 202 of the elongated hollow tube 114 preferably has a scale on its outer surface for measuring the quantity of cervical agent(s) inside the internal chamber 210 of the elongated hollow tube 114. After introducing the desired amount of cervical agent(s) into the elongated hollow tube 114, the user removes the cervical agent tube and replaces it with the cervical cap 102. The CID 100 then is inserted through a patient's vagina, either alone or with the aid of a speculum. The elongated rod 116 is slid forward through the interior chamber 210 of the elongated hollow tube 114 such that the first and second expelling surfaces 310, 312 force the cervical agent(s) from the syringe 110 into the cervical cap 102 and into contact with the patient's cervix. The tapering of the elongated hollow tube 114 and/or the use of ridges 618 assists and facilitates in regulating the speed and amount of therapeutic agent.

The cervical cap 102 makes drug delivery to the cervix more efficient because the cervical cap 102 prevents the drug from leaking from the area and from being absorbed by surrounding tissues. As a result, the cervical treatment should be more effective because the cervix has been exposed to a more concentrated dose of drug than it otherwise would have been had the cervical cap 102 not been used.

In an alternative embodiment in which the object is to harvest cells from the patient's cervix, an elongated rod 500 having a means for harvesting cells 502 is used. The CID 100 is inserted through the patient's vagina such that the cervical cap 102 encompasses the patient's cervix just as described above. The elongated rod 500 is slid forward within the interior chamber 210 of the elongated hollow tube 114 and the harvesting means 502 is used to scrape or rub cells from the cervix by rotating the elongated rod 116. The CID 100 is then removed from the patient, and a cap cover 402 is secured over the front opening 108 of the cervical cap 102 thereby containing the brush 506 with the collected cells safely within the cervical cap 102. The CID 100 may then be forwarded to a hospital, healthcare facility, or lab for analysis.

Performance Results:

Experiments using the CID 100 of the present invention have been performed in women who have been selected to undergo an abdominal hysterectomy. The experiments were performed to determine the ability of the CID 100 to deliver a therapeutic drug to a patient's cervix and whether that drug is absorbed across the cervix into the uterine and peripheral circulation. In each test, a patient is placed under general anesthesia, the abdominal cavity is surgically opened, and the uterine artery and vein are isolated. The CID 100, having a cervical cap 102 pre-filled with 5 mg of diazepam in a lubricating jelly, is inserted into the patient's vagina via a speculum, and the cervical cap 102 is placed over the patient's cervix. The medication is administered and timing is begun. At 1, 5, 10, 15 and 30 minute intervals following drug administration, blood sampling is performed from the uterine artery, the uterine vein, and a peripheral vein (in the arm). Additionally, a blood sample is taken from the uterine vein at 30 minutes. Samples are collected in a tube containing EDTA and subsequently centrifuged to remove the plasma. The samples are then stored at −20° C. At a later point in time, the plasma samples are thawed for analysis of diazepam concentrations. Diazepam and its metabolite, nordiazepam, are measured by liquid chromatography-mass spectrometry. Concentrations of diazepam and nordiazepam measured at the various sampling sites and at the various time points are presented in Table 1.

TABLE 1

| ID # | Sample Description | Diazepam (ng/mL) | Nordiazepam (ng/mL) |
|---|---|---|---|
| Control | Blank Plasma | not detectable | not detectable |
| Patient 1 | | | |
| D1-1 | Uterine vein - 1 minute | 1.9 | 2.8 |
| D1-2 | Uterine artery - 1 minute | 0.6 | 1.6 |
| D1-3 | Uterine vein - 5 minutes | 3.1 | 1.2 |
| D1-4 | Uterine artery - 5 minutes | 2.7 | 0.9 |
| D1-5 | Peripheral vein - 1 minute | 4.6 | 1.2 |
| D1-6 | Peripheral vein - 5 minutes | 2.6 | 1.1 |
| Patient 2 | | | |
| D6-31 | Uterine Vein - 30 minutes | 238.7 | 1.4 |
| D6-33 | Peripheral Vein - 5 minutes | 3.4 | 3.0 |
| D6-34 | Peripheral Vein - 10 minutes | 6.1 | 2.7 |
| D6-35 | Peripheral Vein - 15 minutes | 8.6 | 3.1 |
| D6-36 | Peripheral Vein - 30 minutes | 27.2 | 3.2 |
| Patient 3 | | | |
| D8-43 | Predose Uterine Vein | not detectable | 86 |
| D8-44 | Uterine Vein 30 minutes | 434.2 | 0.86 |
| D8-45 | Uterine Tissue 35 minutes | 221.4 | 1.1 |
| D8-46 | Peripheral Vein 5 minutes | 8.2 | 1.1 |
| D8-47 | Peripheral Vein 10 minutes | 14.8 | 1.4 |
| D8-48 | Peripheral Vein 15 minutes | 15.2 | 1.4 |
| D8-49 | Peripheral Vein 30 minutes | 9.3 | 1.6 |

Thus, as Table 1 shows, the CID 100 successfully delivers a therapeutic drug to the patient's cervix and that drug crosses the cervix and enters the uterine and peripheral circulation.

CONCLUSION

While various embodiments of the present invention have been described above, it should be under-stood that they have been presented by way of example only, and not limitation. It will be understood by those skilled in the art that various changes in form and details may be made therein without departing from the spirit and scope of the invention as defined in the appended claims. Thus, the breadth and scope of the present invention should not be limited by any of the above-described exemplary embodiments, but should be defined only in accordance with the following claims and their equivalents.

What is claimed is:

1. A method for harvesting cells from a patient's cervix, comprising the steps of:
    (a) inserting a cervical isolation and delivery apparatus into a patient's vagina, said cervical isolation and delivery apparatus comprising:
        an elongated hollow tube having an internal chamber, an application end, and a front end;
        an elongated rod being a cylindrical body having an application end having a means for harvesting cells, and an engaging end, said elongated rod being slidably disposed within said internal chamber of said elongated hollow tube with said application end of said elongated rod positioned toward said application end of said elongated hollow tube and said engaging end of said elongated rod positioned toward said front end of said elongated hollow tube, wherein said elongated rod is in an extended position within said elongated hollow tube when said application end of said elongated rod is in proximity to said front end of said elongated hollow tube and is in a retracted position within said elongated hollow tube when said application end of said elongated rod is in proximity to said application end of said elongated hollow tube; and
        a cervical cap having a front opening, a bottom opening, and a means for connecting said cervical cap to said application end of said elongated hollow tube such that said internal chamber of said elongated hollow tube is in communication with said bottom opening of said cervical cap;
    (b) positioning said front opening of said cervical cap of said cervical isolation and delivery apparatus over the patient's cervix;
    (c) sliding said elongated rod through said elongated hollow tube such that said means for harvesting cells of said elongated rod slides from said internal chamber of said elongated hollow tube into said cervical cap and in contact with the patient's cervix; and
    (d) harvesting cells from the patient's cervix.

2. The method according to claim 1, wherein said means for harvesting cells is connected to said application end of said elongated rod and is adapted for passing through said bottom opening of said cervical cap.

3. The method according to claim 1, wherein said means for harvesting cells is selected from the group consisting of a brush, a spatula, and a swab.

4. The method according to claim 1, wherein said step (d) comprises rotating said elongated rod within said elongated hollow tube such that said means for harvesting cells remains in contact with the patient's cervix.

5. The method according to claim 1, further comprising the steps of:
    (e) removing said cervical isolation and delivery apparatus from the patient's vagina; and
    (f) covering said front opening of said cervical cap with a cap cover.

6. The method according to claim 1, further comprising the step of:
    (e) analyzing the cells harvested from the patient's cervix.

* * * * *